United States Patent
Khemliche et al.

(10) Patent No.: US 8,232,518 B2
(45) Date of Patent: Jul. 31, 2012

(54) DEVICE AND METHOD FOR CHARACTERIZING SURFACES

(75) Inventors: Hocine Khemliche, Viry-Chatillon (FR); Philippe Roncin, Gif-sur-Yvette (FR); Patrick Rousseau, Viry-Chatillon (FR)

(73) Assignees: Centre National de la Recherche Scientifique (CNRS), Paris (FR); Universite Paris SUD 11, Cedex (FR)

( * ) Notice: Subject to any disclaimer, the term of this patent is extended or adjusted under 35 U.S.C. 154(b) by 266 days.

(21) Appl. No.: 12/307,816
(22) PCT Filed: Jul. 5, 2007
(86) PCT No.: PCT/FR2007/001146
§ 371 (c)(1), (2), (4) Date: May 4, 2009
(87) PCT Pub. No.: WO2008/003865
PCT Pub. Date: Jan. 10, 2008

(65) Prior Publication Data
US 2009/0250600 A1    Oct. 8, 2009

(30) Foreign Application Priority Data
Jul. 7, 2006 (FR) ..................... 06 06211

(51) Int. Cl.
*G21K 5/04* (2006.01)
(52) U.S. Cl. ............. 250/251; 250/305; 250/492.1
(58) Field of Classification Search ............ 250/251, 250/306, 307, 309, 310, 311
See application file for complete search history.

(56) References Cited

U.S. PATENT DOCUMENTS
5,883,005 A * 3/1999 Minton et al. ............ 438/707
2003/0066749 A1* 4/2003 Golovchenko et al. .. 204/192.32

FOREIGN PATENT DOCUMENTS
EP    1 401 007 A1    3/2004

OTHER PUBLICATIONS

International Search Report and Written Opinion for PCT/FR2007/001146 filed Jul. 5, 2007.
Database Inspec [Online]; The Institution of Electrical Engineers, Stevenage, GB; Sep. 15, 1985; Pimbley J M et al: "Integral representation of the diffracted intensity from one-dimensional stepped surfaces and epitaxial layers"; XP002439157; Database Accession No. 2571642.
Database Inspec [Online]; The Institution of Electrical Engineers, Stevenage, GB; Dec. 27, 2003; Kawasuso A et al: "Top most surface studies by total reflection positron diffraction"; XP002439158; Database Accession No. 8250148.

* cited by examiner

Primary Examiner — David A Vanore
Assistant Examiner — Nicole Ippolito
(74) Attorney, Agent, or Firm — Alston & Bird LLP (57) ABSTRACT

A method of characterizing surfaces comprises the steps of:
  directing a beam (2) of neutral atoms or molecules on a surface (3) for characterizing; and
  detecting in position-sensitive manner the neutral atoms or molecules of said beam that have been diffused forwards by said surface (3) for characterizing;
the properties of said beam (2) being selected in such a manner that at least some of said neutral atoms or molecules that are diffused forwards are diffractive by said surface for characterizing.
A device for implementing such a method comprises means (1) for generating such a beam (2) of neutral atoms or molecules and position-sensitive detector means (4) for detecting the neutral atoms or molecules that are diffused forwards by said surface (3) for characterizing.

25 Claims, 3 Drawing Sheets

DEVICE AND METHOD FOR CHARACTERIZING SURFACES

CROSS REFERENCE TO RELATED APPLICATIONS

This application is a national stage application filed under 35 U.S.C. 371 of International Application No. PCT/FR2007/001146, filed Jul. 5, 2007, which claims priority from French Application No. 06 06211, filed Jul. 7, 2006.

FIELD AND BACKGROUND OF THE INVENTION

The invention relates to a device and a method for characterizing surfaces. It serves in particular to determine the crystallographic structure of crystal surfaces and to perform real-time monitoring crystal growth by molecular beam epitaxy.

The techniques most commonly used for determining the crystallographic structure of surfaces are slow electron diffraction also known as low energy electron diffraction (LEED), and diffraction by reflecting fast electrons also known as reflection high energy electron diffraction (RHEED). In particular, the RHEED technique presents the major advantage of being compatible with growing crystals by molecular beam epitaxy; as a general rule, molecular beam epitaxy apparatuses include an incorporated RHEED device. The device is constituted essentially by an electron gun arranged to produce a substantially monokinetic beam of electrons having energy of the order of 5 kiloelectron volts (keV) to 50 keV directed towards the surface under study at an angle of incidence of about 1° to 4° relative to the plane of the surface, a phosphorus screen for viewing electrons that are diffracted forwards by the surface, and a camera for acquiring images of said phosphorus screen.

The RHEED technique makes it possible to characterize the crystallographic structure of a surface completely, providing corresponding acquisitions are performed at least two distinct orientations of said surface. Nevertheless, characterization is very often limited to qualitative characterization of the state of a surface in comparison with a reference diffraction pattern. Another important application of the RHEED technique is real-time monitoring of the layer by layer growth of a crystal by molecular beam epitaxy. Once a layer has been completed, the diffraction peaks are clearly visible and present high contrast; as additional atoms become deposited on said layer, contrast worsens and begins to increase again when these atoms become sufficiently numerous to form a new layer. Oscillations are thus observed in the diffraction signal, thereby making it possible to track in real time the formation of the various layers of atoms of the crystal.

Although its advantageous properties have made the RHEED technique an industrial standard, it nevertheless presents certain drawbacks.

Firstly, even at grazing incidence, electrons present penetration power of several angstroms (Å), which means that they are sensitive not only to the first layer of atoms that strictly speaking constitute the surface, but they are also sensitive to the initial underlying layers. Furthermore, the penetration of electrons under the surface often gives rise to a diffraction pattern that is complex and that is difficult to interpret.

In addition, electron diffraction techniques (not only RHEED, but also LEED) are poorly adapted to characterizing insulating materials, since they induce a surface charge that can influence the primary beam itself and thus interfere with the diffraction pattern. Worse still, the inelastic interactions between the electrons and the surface generally damage the surface and can radically disturb the growth of insulating films. That is why those techniques do not enable the growth of insulating layers to be monitored on line, but are used rather as destructive testing techniques when devising fabrication protocols.

Given the importance of insulating layers, and in particular of oxides, in microelectronics, that is a major limitation of the technique.

In order to characterize surfaces crystallographically, it is also known to use lightweight atoms, generally of He, presenting energy of the order of a few tens or a few hundreds millielectron volts (meV) and directed perpendicularly or obliquely to the surface under study, generally at an angle of incidence lying in the range 40° to 60° relative to the plane of the surface. That technique, known as helium atom scattering (HAS) or as thermal energy atom scattering (TEAS) presents the advantage of being sensitive solely to the first layer of atoms on the sample under study, the penetrating power of low-energy atoms being negligible, and therefore not inducing and charging of insulating surfaces. Nevertheless, it is used only very rarely in industry since it presents major drawbacks.

Firstly, it is not compatible with growth by molecular beam epitaxy, which requires a large amount of space above the surface to remain empty in order to allow molecular beams to pass. Unfortunately, in order to implement the HAS/TEAS technique, it is specifically necessary to provide a source of thermal atoms not far from the normal to the surface; that technique therefore generally allows ex-situ analysis only. The LEED technique also shares this drawback, which explains why the LEED technique is less popular than the RHEED technique, even though it is superior in terms of the quality of the diffraction patterns that are obtained.

Secondly, generating beams of low-energy atoms requires the use of equipment that is heavy and bulky (supersonic jets, differential pumping stages, etc.).

Thirdly, low-energy neutral atoms are extremely difficult to detect. Detection is generally performed point by point using a mass spectrometer that is moved in two dimensions. Building up a diffraction pattern therefore requires a considerable length of time, which is not compatible with in-line monitoring.

In practice, that technique is used almost exclusively in the laboratory.

It is also known to study the structure of surfaces with the help of atoms or ions that are weakly charged and that present relatively high energy (several kiloelectron volts) at grazing incidence. Under such conditions, the projectiles behave essentially like conventional particles and they are reflected by the surface potential at a great distance from the first layer of atoms. The diffusion profile gives access indirectly to the shape of the interaction potential between the projectile and the first layer of the surface. For more details about that method of characterizing a surface, reference can be made to the article by A. Schüller et al. "Dynamic dependence of interaction potentials for keV atoms at metal surfaces", Phys. Rev. A, 69, 050901 (R), 2004.

The drawback of that technique is that the diffusion profiles are difficult to interpret and they are always less rich in information than the profiles obtained by diffraction techniques that make use of the wave nature of the projectiles.

SUMMARY OF THE INVENTION

An object of the present invention is to remedy at least some of the drawbacks of the prior art.

More specifically, an object of the invention is to provide a technique of characterizing a surface that presents increased sensitivity to the first layer of atoms compared with the RHEED and LEED techniques.

Another object of the invention is to provide a characterization technique that is better adapted to insulating surfaces than are the techniques known in the prior art.

Yet another object of the invention is to provide a technique for characterizing surfaces that is compatible with growth by electron beam epitaxy and that enables said growth to be monitored in real time.

Yet another object of the invention is to provide a technique of characterizing surfaces that is simple to implement, not only in the laboratory, but also in an industrial environment.

At least one of the above objects is achieved by a device for characterizing surfaces that comprises:
    means for generating a beam of neutral atoms or molecules, the means being arranged to direct said beam towards a surface for characterizing; and
    detector means that are sensitive to position for detecting the neutral atoms or molecules of said beam that have been diffused forwards by said surface for characterizing;
    the device being characterized in that:
    said means for generating a beam of neutral atoms or molecules are adapted to produce a beam having energy lying in the range 50 electron volts (eV) to 5 keV with divergence no greater than 0.05°; and
    said means for generating a beam of neutral atoms or molecules are adapted to direct said beam towards said surface for characterizing at an angle of incidence no greater than 10° relative to the plane of said surface;
in such a manner that a diffraction pattern of said neutral atoms or molecules diffused forwards by said surface for characterizing is detectable by said position-sensitive detector means.

In particular embodiments of the device of the invention:
    Said means for generating a beam of neutral atoms or molecules may be adapted to produce a beam having energy lying in the range 100 eV to 1 keV, preferably in the range 100 eV to 700 eV.
    Said means for generating a beam of neutral atoms or molecules may be adapted to produce a beam having energy lying in the range 100 eV to 2 keV, preferably in the range 100 eV to 1 keV.
    Said means for generating a beam of neutral atoms or molecules may be adapted to produce a beam having energy dispersion no greater than 5%.
    Said means for generating a beam of neutral atoms or molecules may be adapted to direct said beam towards said surface for characterizing with an angle of incidence lying in the range 0.5° to 3°, relative to the plane of the surface.
    The angle of incidence and the energy of said beam of atoms or molecules may be selected in such a manner that the energy associated with movement in a direction perpendicular to the surface is less than or equal to 1 eV.
    Said means for generating a beam of neutral atoms or molecules are adapted to generate a beam constituted by particles having atomic mass lying in the range 1 atomic unit (au) to 20 au, and more particularly constituted by a chemical species selected from H, $H_2$, and $^3$He, or isotopes thereof.
    Said means for generating a beam of neutral atoms or molecules may comprise: means for generating a beam of atomic or molecular ions; means for neutralizing said beam of atomic or molecular ions; and means for collimating the beam of neutral atoms or molecules obtained by neutralizing said beam of atomic or molecular ions.
    Said means for generating a beam of neutral atoms or molecules also may comprise means for filtering said atomic or molecular ions by mass.
    Said means for generating a beam of neutral atoms or molecules may comprise chopper means for generating a pulsed beam.
    Said position-sensitive detector means may also present time sensitivity, with resolution of not more than 50 nanoseconds (ns), and preferably not more than 10 ns, so as to determine the energy loss of the neutral atoms or molecules of said beam as a result of being diffused by said surface, by measuring flight time.
    The device may also comprise secondary detector means for detecting neutral or ionized atoms or molecules, said secondary detector means having time resolution no greater than 1 microseconds (µs), preferably no greater than 100 ns, and even more preferably no greater than 10 ns, and being arranged in such a manner as to detect neutral or ionized atoms or molecules that leave the surface for characterizing on a trajectory that forms relative to said surface an angle that is greater than the specular reflection angle of said beam of neutral atoms or molecules.

The invention also provides a molecular jet epitaxy machine including a surface characterization device as defined above, arranged to characterize the surface of a crystal that is being grown.

The invention also provides a method of characterizing surfaces, the method comprising the steps of:
    directing a beam of neutral atoms or molecules on the surface to be characterized; and
    detecting in position-sensitive manner the neutral atoms or molecules of said beam that have been diffused forwards by said surface for characterizing;
    the method being characterized in that:
    said beam of neutral atoms or molecules has energy lying in the range 50 eV to 5 keV, and divergence no greater than 0.05°; and
    the angle of incidence of said beam on said surface for characterizing is no greater than 10° relative to the plane of said surface;
in such a manner that at least some of said forwardly-diffused neutral atoms or molecules are diffracted by said surface for characterizing.

In particular implementations of the method of the invention:
    Said beam of neutral atoms or molecules may present energy lying in the range 100 eV to 1 keV, and preferably in the range 100 eV to 700 eV.
    Said beam of neutral atoms or molecules may present energy lying in the range 100 eV to 2 keV, and preferably in the range 100 eV to 1 keV.
    Said beam of neutral atoms or molecules may present energy dispersion no greater than 5%.
    The angle of incidence of said beam on said surface for characterizing may lie in the range 0.5° to 3°, relative to the plane of the surface.
    The angle of incidence and the energy of said beam of atoms or molecules may be selected in such a manner that the energy associated with movement in a direction perpendicular to the surface is less than or equal to 1 eV.
    Said beam may be constituted by particles presenting atomic mass lying in the range 1 au to 20 au, and in particular a chemical species selected from H, $H_2$, or $^3$He, and isotopes thereof.

The method may also include a step for determining at least one crystallographic parameter of said surface for characterizing from a detected diffraction pattern of said neutral atoms or molecules diffused forwards by said surface for characterizing.

The method may be implemented during fabrication of a crystal by molecular beam epitaxy, the method also including: a step of observing oscillatory behavior over time of said diffraction pattern; and a step of extracting information relating to the epitaxial growth of successive layers of atoms forming said crystal on the basis of said observation of oscillatory behavior over time of said diffraction pattern.

BRIEF DESCRIPTION OF THE DRAWINGS

Other characteristics, details, and advantages of the invention appear on reading the following description made with reference to the accompanying drawings given by way of example and, in which.

MORE DETAILED DESCRIPTION

Figure 1A:
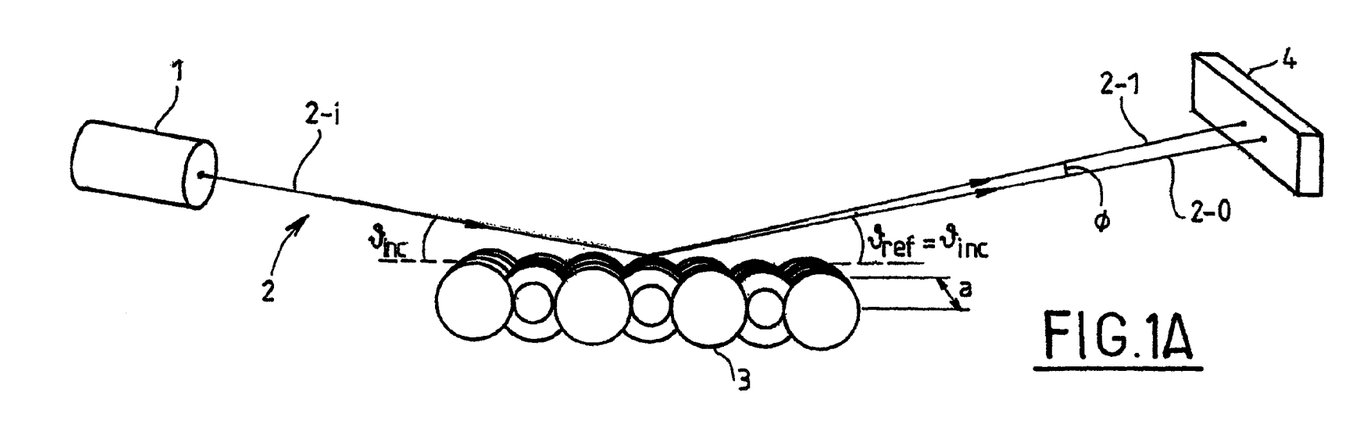
FIG. 1A is a general diagram of a device and a method of the invention.

As shown in FIG. 1A a device of the invention essentially comprises means 1 for generating a beam 2 of neutral atoms or molecules, and position-sensitive detector means 3 for detecting said beam of neutral atoms or molecules.

The beam 2 is directed towards a surface 3 for characterizing at an angle of incidence $\theta_{inc}$ that is optionally variable, and not greater than about 10° (grazing incidence); here and below, angles are measured relative to the plane of the target surface 3. As in the RHEED technique, the space immediately above the surface 3 remains unencumbered, thereby making it possible in particular to perform electron beam epitaxial growth simultaneously with taking a measurement.

The neutral atoms or molecules of the beam 2 are reflected by the surface 3 at a reflection angle $\theta_{ref} \approx \theta_{inc}$; simultaneously they are subjected to diffraction in an azimuth direction, i.e. parallel to the surface 3. In FIG. 1, the incident atom or molecule beam is given reference 2-$i$, the specular beam is given reference 2-0 (since it constitutes "zero" order diffraction), and the first non-specular beam is referenced 2-1 (first order diffraction). As in RHEED, the angle $\theta$ formed by projecting the first order diffracted beam 2-1 and the zero order diffracted beam 2-0 onto a plane parallel to the plane of the surface 3 is associated with the lattice parameter a of the crystal surfaces 3 in the direction that extends transversely relative to the movement of the incident atoms or molecules.

Figure 1B:
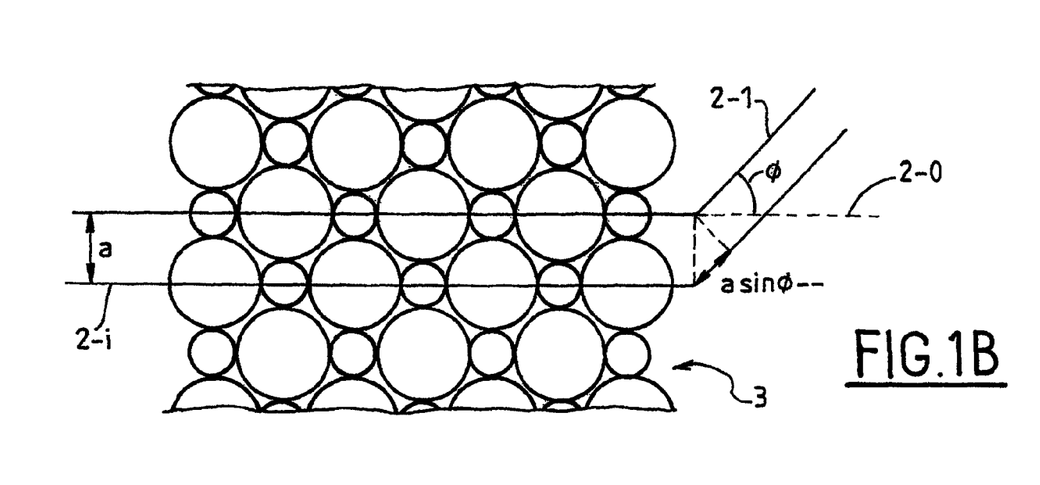
FIG. 1B illustrates the Bragg conditions for a wave to be diffracted by a crystal.

This association is given by the Bragg equation, represented graphically in FIG. 1B:

$$\alpha \sin \theta = n\lambda$$

where n is an integer, from which it can be deduced:

$$\phi = \arcsin\left(\frac{\lambda}{\alpha}\right)$$

for the first diffraction order, where $\lambda$ is the de Broglie wavelength of the incident particles.

Under grazing incidence conditions, it is possible to consider that the movement of the particles in a direction normal to the surface 3 is decoupled from their longitudinal movement parallel to said surface 3, and that what is observed is the result of the normal component of the wave of material being diffracted by the surface potential transverse to the movement. Thus, even when the total energy $E_0$ of the particle is of keV order, its normal energy $$E_n = E_0 \sin^2 \theta_{inc}$$

may be less than 1 eV, which corresponds to a normal wavelength $$\lambda_n = \frac{h}{\sqrt{2mE_n}}$$

(where h is Planck's constant and m is the mass of said particles), which is of the same order of magnitude as the lattice parameters a to be measured. For example, with hydrogen atoms H having an energy of 500 eV and an angle of incidence of 1.4°, it is found that $E_n$=0.3 eV, which corresponds to a normal wavelength $\lambda$=0.53 angstroms (Å), which should be compared with the lattice parameter of a surface such as that of NaCl, where a=5.64 Å.

The diffracted beams 2-0 to 2-1 are detected at a distance from the surface 3 by the position-sensitive means 4, thereby forming an image of the diffraction pattern, thus enabling the angle $\phi$ to be measured, and consequently enabling the lattice parameter a to be determined. Unlike what happens with thermal atoms in the HAS/TEAS technique, the high-energy particles used in the method of the invention can be detected simply, e.g. by means of microchannel plates (MCP) coupled to a phosphorus screen which is in turn imaged by a CCD camera.

Naturally, FIG. 1A constitutes a simplification, since in general several diffraction orders are observed simultaneously, together with an incoherent background due to defects in the structure of the surface (steps, adsorbed atoms, etc.), and also to thermal vibration.

Figure 2:
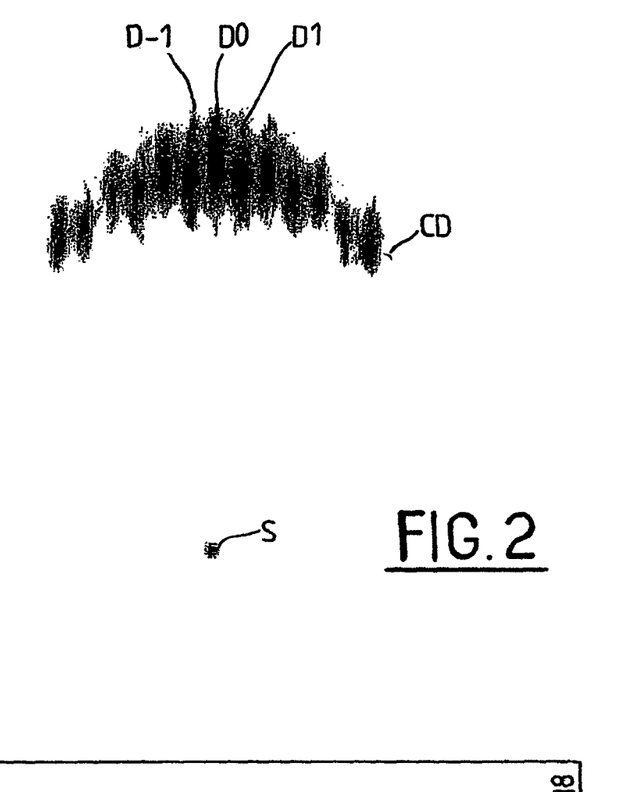
FIG. 2 is an example of a diffraction diagram of atoms at a grazing angle of incidence, as obtained by the method of the invention.

FIG. 2 shows a real example of a diffraction pattern obtained by directing $H_2$ molecules with energy of 400 eV onto a ZnSe (001) surface in the [1-1 0] crystallographic direction with an angle of incidence of 1.1°. Several diffraction orders can be seen; references D0, D−1, and D1 reveal the central spot corresponding to the zero order and to the two first orders located symmetrically on either side thereof. The spacing between the diffraction spots provides information about the periodicity of the crystal lattice of the surface (lattice parameter a), as is true in all diffraction techniques, see for example the work by D. P. Woodruff and T. A. Delchar "Modern techniques of surface science", Cambridge University Press, 1986, while the intensity of the spots provides information about the form of the interactive potential between the projectile and the surface. It can be seen that the diffraction spots are disposed along a curve CD of shape that depends on the form of said interaction potential, on the normal energy $E_n$ of the projectile, and on temperature. For a non-reactive projectile, the curve CD is a circular arc of center lying on the projected plane of the surface.

It is possible to study the structure of the potential of the surface finely by observing variation in the relative intensity of the diffraction peaks and the shape of the curve CD with angle of incidence $\theta_{inc}$ ("rocking curves"). The inversion techniques that enable the surface potential to be reconstructed from these observations are essentially the same as those used when studying the diffraction of thermal neutral atoms, see for example the article by R. I. Masel et al., "Quantum scattering from a sinusoidal hard wall: atomic diffraction from solid surfaces", Phys. Rev. B, 12, 5545, 1975.

In the bottom portion of FIG. 2, there can be seen a spot S produced by the particles of the beam 2 that have flown over the surface 3 without interacting. Observation of the spot S does not provide any information that is directly associated with the properties of said surface, but it can be used to determine the angles of incidence and of diffusion, and to calibrate the loss of energy in flight-time measurements when using a pulsed beam.

In general, it is possible to observe a diffraction pattern that is usable for crystallographic purposes only if working conditions are selected appropriately, and in particular the nature and the energy of the particles constituting the beam 2, the angle of incidence $\theta_{inc}$ of said beam on the surface 3, and the divergence and the width of the beam. Preferably, these working conditions are selected in such a manner that the Bragg peaks are clearly resolved. Nevertheless, even if the normal energy of the projectiles is increased a little beyond the point where Bragg peaks are no longer resolved, an interference pattern remains in the form of low frequency spatial modulation of the diffusion profile; this incompletely resolved diffraction pattern still provides information that is characteristic of the form of the surface potential.

Concerning the nature of the projectile, it is possible to use atoms or small particles of mass lying in the range 1 atomic unit (H) to 20 atomic units ($^{20}$Ne). Lightweight projectiles are generally preferred, since for given energy they have a longer wavelength. In particular, H, $H_2$, and $^3$He and their isotopes are found to constitute particularly advantageous choices. H is the projectile of lowest mass and using it enables the interaction potential of the surface with hydrogen to be studied, which is of great interest in numerous applications. $^3$He is preferred when it is desired to have a projectile that is chemically inert, while $H_2$, of mass and reactivity that are intermediate between the masses and reactivities of H and of $^3$He, can constitute a compromise solution. In general, He ($^3$He or $^4$He) constitutes the preferred projectile.

The energy $E_0$ of the beam may lie in the range about 50 eV about to 5 keV, preferably in the range 100 eV to 2 keV, and even more preferably in the range 100 eV to 1 keV. It is preferable for the energy dispersion of the beam to be less than or equal to 5%, preferably less than or equal to 2%.

The angle of incidence relative to the plane of the surface, $\theta_{inc}$, should be less than or equal to 10°, and should preferably lie in the range 0.5° to 3°.

The energy and the angle are parameters that are not strictly independent: it is preferable for the normal energy $$E_n = E_0 \sin^2 \theta_{inc}$$

to be less than or equal to 1 eV.

The divergence of the beam should be minimized since it tends to make the diffraction peaks fuzzy: typically, in order to obtain images of good quality, it is necessary to obtain divergence that is not greater than 0.05°.

It is also advantageous for the size of the beam to be less than or equal to 1 millimeter (mm), preferably to lie in the range about 10 micrometers (μm) to 300 μm. The size of the beam in a direction parallel to the surface has a direct influence on the diffraction spots on the detector 3; if the beam is too wide, the spots tend to superpose making the diffraction pattern fuzzy. The width of the beam in a direction normal to the surface is less critical, but it should be understood that because of the grazing incidence, the projection on the surface of this dimension of the beam is stretched by a factor of $1/\sin \theta_{inc}$, which can therefore easily exceed the size of the sample. It is therefore preferable likewise to limit this width to a value less than or equal to 1 mm. As a general rule, it is preferable to use beams having a section that is at least approximately circular.

The flux need not necessarily be very great: with a flux of no more than a few hundreds of atoms per second, an exposure of a few minutes suffices for obtaining images that are directly usable.

The temperature of the sample is another parameter that needs to be taken into consideration, since the thermal agitation of the surface atoms has a negative influence on the effectiveness of diffraction. It is therefore advantageous for the sample to be maintained at ambient temperature (around 300 K) during measurement. It is generally not necessary to cool the samples to cryogenic temperatures, even though that can improve the quality of the resulting diffraction pattern. If a temperature is imposed, e.g. by the epitaxial growth process, then it is possible to limit the effect of thermal agitation by selecting a smaller angle of incidence: the closer the incidence is to grazing, the more diffusion takes place at a distance from the surface, and thus the smaller the sensitivity of the projectile to defects of periodicity induced by the thermal agitation.

Figure 3A:
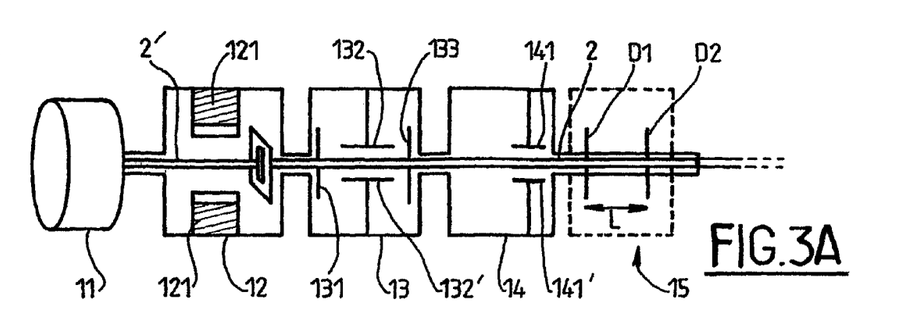
FIGS. 3A and 3B are diagrams of means for generating an atom beam respectively in a first embodiment and in a second embodiment of the invention.

Means for generating a beam of ions or molecules suitable for implementing the invention are shown in FIG. 3A. The device is constituted essentially by a beam generator 2' for generating a beam of atomic or molecular ions 11, a neutralizer 14, and a collimator 15.

Several types of ion source 11 suitable for implementing the invention are commercially available, and they deliver ion beams of energy lying in the range a few eV to a few keV. As an example, mention can be made of electron cyclotron resonance (ECR) sources, and of discharge sources. The ion source 11 comprises a set of electrodes for accelerating ions to the desired energy by applying an electrostatic field, together with an electrostatic focusing system.

If the ion beam generated by the source 11 is not sufficiently pure from a chemical and isotopic point of view, or if it contains ions having different states of charge, it can be directed towards a mass filter 12 that uses a magnetic field generated by a magnet 121 and a slit 122 to select particles having a determined ratio of mass over charge. Although not visible in FIG. 3A, a magnetic mass filter of this type is not in a straight line and necessarily deflects the ion beam 2'.

In a variant, it is possible to use a Wien filter or any other appropriate mass filter.

If it is desired to obtain a pulsed beam, it is possible to provide a stopper 13 either upstream or downstream of the mass filter, if any. In an embodiment of the invention, the device has an inlet slit 131 for shaping the beam, two plate electrodes 132 and 132' facing each other, and an outlet orifice 133. By applying a varying electric field to the electrodes 132 and 132', the ion beam is caused to sweep over the outlet orifice; if the field applied to the electrodes is periodic, then a pulsed outlet beam is obtained.

The electric charge of the ions enables them to be accelerated, selected, and pulsed much more easily than neutral particles. The ion beams 2' can then be neutralized by exchanging charge in a cell 14 filled with gas. Ideally, the gas used in the cell 14 is constituted by the same chemical species as the beam 2 so as to optimize charge exchange by resonant capture; the pressure $P_{14}$ inside the cell depends on its length $L_{14}$, and in general the following is imposed:

$$P_{14} \times L_{14} \leq 10^{-3} \text{ millibar centimeters (mbar·cm)}$$

At the outlet from the cell 14, an electrostatic field applied by the electrodes 141 and 141' serves to deflect the remaining ions so that only a beam 2 of neutral atoms or molecules leaves the cell 14.

The beam of atoms or molecules leaving the neutralizer 14 presents divergence that is too great for it to be possible to observe diffraction by the target surface 3, so the beam needs to be collimated. A collimator 15 may be constituted merely by first and second diaphragms D1 and D2 that are preferably circular, having diameters $\varnothing_{D1}$ and $\varnothing_{D2}$, of the same order of magnitude, being in alignment on the axis of the beam and spaced apart by a distance L. Simple geometrical considerations show that the divergence of the outlet beam, defined as being equal to the half-angle at the apex, is given by:

$$\text{Div} = (\varnothing_{D1} + \varnothing_{D2})/2L$$

By way of example, $\varnothing_{D1}$ and $\varnothing_{D2}$ can be taken to be about 100 µm to 200 µm, and L can lie in the range 20 centimeters (cm) to 30 cm.

Figure 3B:
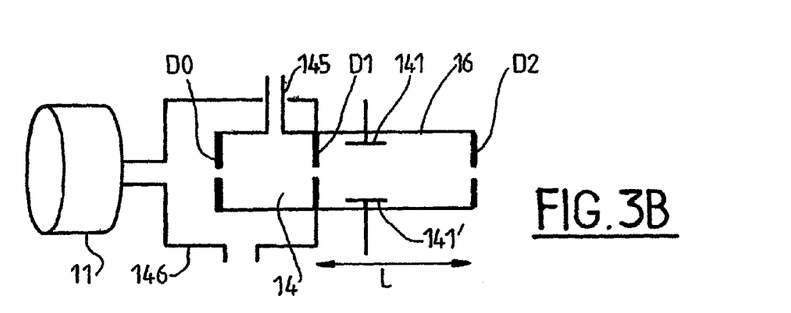

FIG. 3B shows a simplified variant that is much more compact of means 1 for generating a beam of atoms or molecules. This simplified device does not have a mass filter 12 nor does it have a chopper 13. In the means 1 for generating a beam of atoms or molecules as shown in FIG. 3B, the neutralization cell 14 is constituted by a section of a tubular element 16 that extends between two diaphragms D0 and D1, with the diameter of the diaphragm D0 being much greater than that of the diaphragm D1. The cell 14 has a gas inlet 145 and is surrounded by an enclosure 146 that is connected to a vacuum pump system (not shown); the electrodes 141 and 141' for deflecting non-recombined ions are located inside said tubular element 16, downstream from the diaphragm D1. In addition to defining the neutralization 14, the diaphragm D1 forms part of the collimator 15, as does the diaphragm D2 situated at the outlet from the tubular element 16. Since it does not include a chopper 13 located upstream from the neutralization cell 14, the device of FIG. 3B cannot produce a pulsed beam 2 of neutral atoms or molecules. Nevertheless, it can produce a pulsed beam of ions 2': to do this, it suffices to evacuate the neutralization cell 14 and to apply a pulsed voltage to the electrodes 141 and 141' so as to use them as a chopper.

Figure 4:
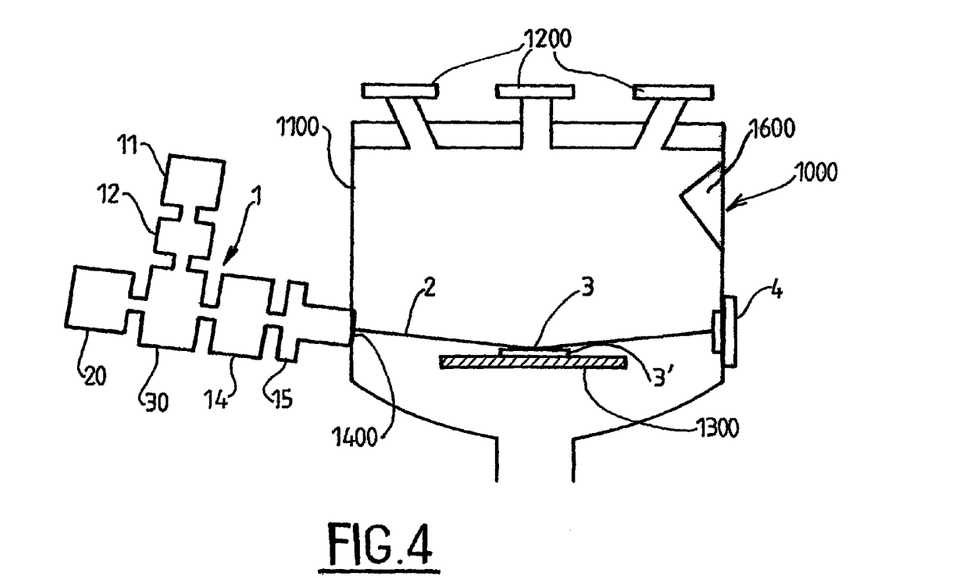
FIG. 4 is a machine for molecular beam epitaxy fitted with a device of the invention.

FIG. 4 shows a molecular beam epitaxy machine 1000 fitted with a device of the invention for characterizing surfaces. The machine 1000 is essentially constituted by an enclosure 1100 connected to a pumping system (not shown) that produces an ultra vacuum. Diffusion cells 1200 open out into the enclosure 1100 and serve to produce beams of molecules. Facing these cells 1200 there is situated a support 1300 for a substrate 3' on which the surface 3 is to be deposited epitaxially.

At an inlet 1400 of the enclosure 1100, there are connected means 1 for generating a high energy beam 2 of atoms or molecules of the type shown in FIG. 3A, but in which the chopper 13 has been replaced by an electrostatic deflector coupled at its inlet likewise to an RHEED electron gun 20. In this way, the user can decide to characterize the surface with the help of the beam 2 of atoms or molecules in accordance with the invention, or by using the traditional RHEED technique, without it being necessary to provide an additional inlet into the enclosure 1100. More precisely, when it is desired to perform RHEED characterization, only the electron gun 20 is activated, while the ion source 11 and the deflector 30 remain inactive, and the neutralization cell 14 is evacuated. Conversely, when it is desired to perform characterization by diffraction of neutral atoms or molecules, the electron gun 20 remains inactive while the ion source 11 and the deflector 30 are active, and the neutralization cell is filled with gas. By periodically activating and deactivating the deflector 30, it is possible to obtain a pulsed beam of atoms or molecules; under such circumstances, the deflector 30 can be used as a chopper.

Detector means 4 that are sensitive to position, constituted by a microchannel plate coupled to a fluorescent screen, are also arranged on the wall of the enclosure 1100, in a position opposite from the generator means 1 relative to the surface 3. The means 4 are also adapted to detecting electrons, and are therefore compatible with the RHEED technique.

In a variant, the characterizing device of the invention can completely replace an RHEED device.

It is most advantageous for the angle of incidence $\theta_{inc}$ of the beam 2 on the surface 3 to be capable of being varied, e.g. over the range 0.5° to 10°, so as to enable said surface to be characterized more completely (the "rocking curve" technique). By way of example, this can be achieved by mounting the generator means 1 on a motor-driven pivot mechanism. In a variant, if all that is required is qualitative inspection of the quality of the surface 3, then the angle $\theta_{inc}$ may be constant.

As explained above, the device of the invention enables the growth of conductive dielectric surfaces to be monitored in real time, whereas the RHEED technique is poorly adapted to dielectric surfaces. Furthermore, the diffraction of fast atoms at grazing incidence makes it possible to obtain diffraction patterns that are easier to interpret than RHEED patterns, because of the low ability of atoms or molecules to penetrate beneath the surface being studied.

However, the device and the method of the invention are not limited to providing information of a crystallographic nature: they can be used for much more complete characterization of surfaces.

Figure 5:
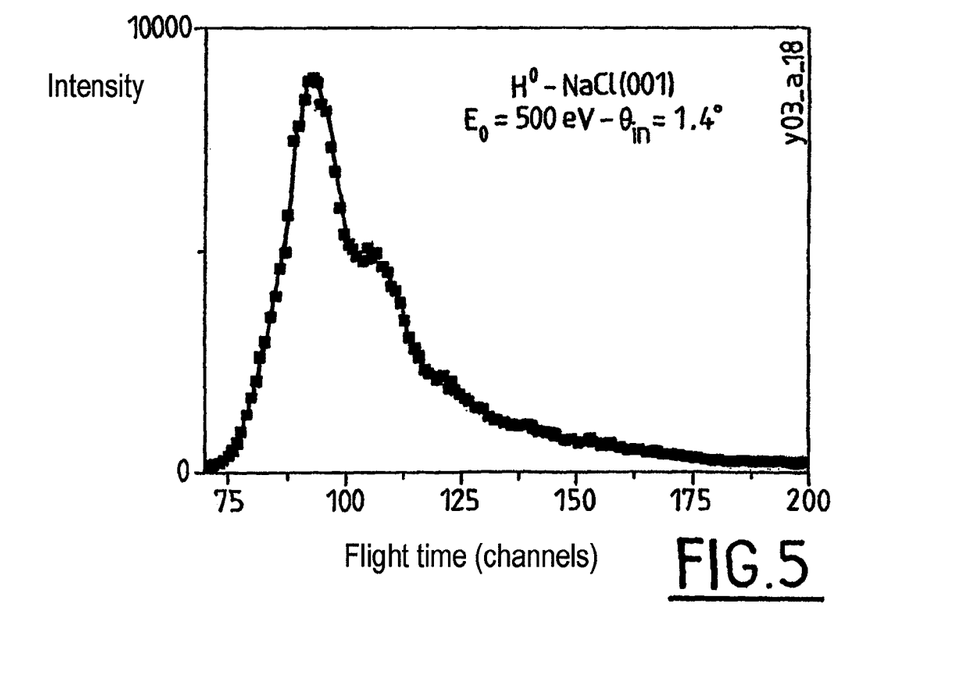
FIG. 5 is a spectrum on the energy loss of neutral particles on being diffused by a surface.

By pulsing the incident beam of atoms with the help of the electrostatic chopper 13 shown in FIG. 3A, it is also possible to study the inelastic diffusion processes between neutral particles and the surface 3. To do this, it is necessary for the detector 4 to present sufficient time resolution to enable the energy of particles diffused by flight time to be measured, e.g. resolution of the order of 50 ns or less, and preferably of the order of 10 ns or less. By way of example, FIG. 5 shows an energy loss spectrum for particles diffused during the interaction of hydrogen atoms having energy of 500 eV with an NaCl (0 0 1) surface, the incidence being in the [1 0 0] crystallographic direction at an angle $\theta_{inc} = 1.4°$. The abscissa axis in FIG. 5 relates to atom flight time, expressed in arbitrary units; the instrument can be calibrated to associate each flight time with a value for the energy of the atoms after being diffused by the surface. Advantageously, it is possible to associate this measurement with detection of electrons that are emitted by the surface during the inelastic interaction.

By way of example, this makes it possible to study the affinity of a surface with atomic hydrogen H used as a projectile. This is important from a technological point of view since H is very easily adsorbed by surfaces and constitutes an obstacle to molecular beam epitaxial growth.

A similar technique can be used to determine the concentration of lightweight particles absorbed by the surface 3. These particles, principally atoms of hydrogen, can be ejected from the surface 3 as a result of a binary collision with the projectiles of the beam 2. Measuring the flight times of these ejected particles serves to determine their masses, and thus to identify them. The heavy particles present on the surface cannot be ejected by the projectiles on the beam 2, since they are much lighter in weight; in contrast, they give rise to diffusion at a large angle with a loss of energy for said projectiles. Under such circumstances, it is measuring the flight time of the deflected projectiles that serves to determine the mass of the absorbed particles, and thus to identify them.

In FIG. 4, a secondary detector serves to measure the flight times of particles ejected from the surface 3 as a result of a collision with a projectile of the beam 2, and also of projectiles of said beam that are diffused at a large angle, as represented diagrammatically by reference 1600. The detector 1600 needs to have time resolution of no more than 1 μs, and preferably of no more than 100 ns, and preferably no greater than 10 ns. In addition, it is arranged to detect neutral or ionized atoms or molecules that leave the surface for characterizing on a trajectory that forms relative to said surface 3 an angle that is greater than the specular reflection angle of the beam of neutral atoms or molecules, e.g. an angle of about 30°.

Adsorbed particles can also be identified by using ions as projectiles. Even in this application, it is possible to use the beam generator means of FIG. 3B that are incapable of producing a pulsed neutral beam.

The above-described techniques for identifying adsorbed particles are themselves known, see for example the following articles:

W. Hayami et al. "Structural analysis of the $HfB_2(0001)$ surface by impact-collision ion scattering spectroscopy", Surface Science 415 (1998) 433-437;

M. Shi et al. "Time-of-flight scattering and recoiling spectrometry. III. The structure of hydrogen on the W(211) surface", Phys. Rev. B, 40, 10163 (1989); and Y. Wang et al. "Structure of the Si{100} surface in the clean (2×1), (2×1)-H monohydride, (1×1)-H dihydride and c(4× 4)-H phases", Phys. Rev. B, 48, 1678 (1993).

Nevertheless, those techniques are generally not used in an industrial environment since they require additional equipment over and above the RHEED analysis device that is always present. By means of the invention, the same means 1 for generating a beam of atoms or molecules can be used equally well for performing surface diffraction measurements and for identifying adsorbed particles. With a negligible increase in the complexity of the instrument (adding the secondary detector 1600), it thus becomes possible to characterize the surface 3 much more completely than is possible by using the RHEED technique alone.

Identifying adsorbed particles is advantageously combined with observing diffraction patterns when performing real-time monitoring of crystal growth by epitaxy. In a particular implementation of the method of the invention, the study of the oscillations of the diffraction peaks makes it possible to follow the progress of the deposition of successive layers of atoms, as is commonly done using the RHEED technique, while detecting particles leaving the surface 3 as a result of a collision with an atom or a molecule of the beam 2 (or an ion of the beam 2'), and projectiles diffused to large angles as a result of a collision with a heavy adsorbed particle, makes it possible to discover the degree of contamination of the same surface. Since chopping the beam 2 or 2' considerably reduces its flux, and therefore makes diffraction patterns difficult to see, the two types of measurement are generally performed in alternation over time.

The invention claimed is:

1. A device for characterizing surfaces, the device comprising:
    means for generating a beam of neutral atoms or molecules, the means being arranged to direct said beam towards a surface for characterizing; and
    detector means that are sensitive to position for detecting the neutral atoms or molecules of said beam that have been diffused forwards by said surface for characterizing;
    wherein:
    said means for generating a beam of neutral atoms or molecules produces a beam having energy lying in the range 50 eV to 5 keV with divergence no greater than 0.05°; and
    said means for generating a beam of neutral atoms or molecules directs said beam towards said surface for characterizing at an angle of incidence no greater than 10° relative to the plane of said surface;
    in such a manner that a diffraction pattern of said neutral atoms or molecules diffused forwards by said surface for characterizing is detectable by said position-sensitive detector means.

2. A device according to claim 1, wherein said means for generating a beam of neutral atoms or molecules produces a beam having energy lying in the range 100 eV to 2 keV.

3. A device according to claim 1, wherein said means for generating a beam of neutral atoms or molecules produces a beam having energy lying in the range 100 eV to 1 keV.

4. A device according to claim 1, wherein said means for generating a beam of neutral atoms or molecules produces a beam having energy dispersion no greater than 5%.

5. A device according to claim 1, wherein said means for generating a beam of neutral atoms or molecules directs said beam towards said surface for characterizing with an angle of incidence lying in the range 0.5° to 3°.

6. A device according to claim 1, wherein the angle of incidence $\theta_{inc}$ and the energy $E_0$ of said beam of atoms or molecules are selected such that $E_0 \sin^2 \theta_{inc} \leq 1$ eV.

7. A device according to claim 1, wherein said means for generating a beam of neutral atoms or molecules generates a beam constituted by particles having atomic mass lying in the range 1 au to 20 au.

8. A device according to claim 7, wherein said means for generating beam of neutral atoms or molecules generates a beam constituted by a chemical species selected from H, $H_2$, and $^3$He, and isotopes thereof.

9. A device according to claim 1, wherein said means for generating a beam of neutral atoms or molecules comprise:
    means for generating a beam of atomic or molecular ions;
    means for neutralizing said beam of atomic or molecular ions; and
    means for collimating the beam of neutral atoms or molecules obtained by neutralizing said beam of atomic or molecular ions.

10. A device according to claim 9, wherein said means for generating a beam of neutral atoms or molecules also comprise means for filtering said atomic or molecular ions by mass.

11. A device according to claim 9, wherein said means for generating a beam of neutral atoms or molecules comprise chopper means for generating a pulsed beam.

12. A device according to claim 11, wherein said position-sensitive detector means also present time sensitivity, with resolution of not more than 50 ns, so as to determine the energy loss of the neutral atoms or molecules of said beam as a result of being diffused by said surface, by measuring flight time.

13. A device according to claim 12, wherein said position-sensitive detector means present time sensitivity, with resolution of not more than 10 ns.

14. A device according to claim 1, also comprising secondary detector means for detecting neutral or ionized atoms or molecules, said secondary detector means having time resolution no greater than 1 µs, and being arranged in such a manner as to detect neutral or ionized atoms or molecules that leave the surface for characterizing on a trajectory that forms relative to said surface an angle that is greater than the specular reflection angle of said beam of neutral atoms or molecules.

15. A machine for molecular jet epitaxy, the machine including a surface characterizing device according to claim 1, arranged to characterize the surface of a crystal that is being grown.

16. A method of characterizing surfaces, the method comprising the steps of:
    directing a beam of neutral atoms or molecules on the surface to be characterized; and
    detecting in position-sensitive manner the neutral atoms or molecules of said beam that have been diffused forwards by said surface for characterizing;
    wherein:
    said beam of neutral atoms or molecules has energy lying in the range 50 eV to 5 keV, and divergence no greater than 0.05°; and
    the angle of incidence of said beam on said surface for characterizing is no greater than 10° relative to the plane of said surface;
    in such a manner that at least some of said forwardly-diffused neutral atoms or molecules are diffracted by said surface for characterizing.

17. A method of characterizing surfaces according to claim 16, wherein said beam of neutral atoms or molecules presents energy lying in the range 100 eV to 2 keV.

18. A method of characterizing surfaces according to claim 17, wherein said beam of neutral atoms or molecules presents energy lying in the range 100 eV to 1 keV.

19. A method of characterizing surfaces according to claim 16, wherein said beam of neutral atoms or molecules presents energy dispersion no greater than 5%.

20. A method of characterizing surfaces according to claim 16, wherein the angle of incidence of said beam on said surface for characterizing lies in the range 0.5° to 3°.

21. A method of characterizing surfaces according claim 16, wherein the angle of incidence $\theta_{inc}$ and the energy $E_0$ of said beam of atoms or molecules are selected such that $E_0 \sin^2 \theta_{inc} < 1$ eV.

22. A method of characterizing surfaces according to claim 16, wherein said beam is constituted by particles presenting atomic mass lying in the range 1 au to 20 au.

23. A method of characterizing surfaces according to claim 22, wherein said beam is constituted by a chemical species selected from H, $H_2$, and $^3$He, and isotopes thereof.

24. A method according to claim 16, also including a step for determining at least one crystallographic parameter of said surface for characterizing from a detected diffraction pattern of said neutral atoms or molecules diffused forwards by said surface for characterizing.

25. A method according to claim 24, implemented during fabrication of a crystal by molecular beam epitaxy, the method also including:
    a step of observing oscillatory behavior over time of said diffraction pattern; and
    a step of extracting information relating to the epitaxial growth of successive layers of atoms forming said crystal on the basis of said observation of oscillatory behavior over time of said diffraction pattern.

* * * * *